US010557792B2

(12) United States Patent
Berman et al.

(10) Patent No.: US 10,557,792 B2
(45) Date of Patent: Feb. 11, 2020

(54) SPECTRAL MODELING FOR COMPLEX ABSORPTION SPECTRUM INTERPRETATION

(71) Applicant: ABB, Inc., Cary, NC (US)

(72) Inventors: Elena S. F. Berman, Mountain View, CA (US); Andrew Fahrland, Sunnyvale, CA (US); Manish Gupta, Mountain View, CA (US); Douglas S. Baer, Menlo Park, CA (US); John Brian Leen, Sunnyvale, CA (US)

( * ) Notice: Subject to any disclaimer, the term of this patent is extended or adjusted under 35 U.S.C. 154(b) by 136 days.

(21) Appl. No.: 14/986,244

(22) Filed: Dec. 31, 2015

(65) Prior Publication Data
US 2017/0191929 A1 Jul. 6, 2017

(51) Int. Cl.
| | |
|---|---|
| G01N 21/39 | (2006.01) |
| G01J 3/457 | (2006.01) |
| G01J 3/00 | (2006.01) |
| G01J 3/42 | (2006.01) |
| G01J 3/28 | (2006.01) |
| G01N 21/35 | (2014.01) |

(52) U.S. Cl.
CPC ............... G01N 21/39 (2013.01); G01J 3/00 (2013.01); G01J 3/28 (2013.01); G01J 3/42 (2013.01); G01J 3/457 (2013.01); *G01J 2003/284* (2013.01); *G01N 2021/3595* (2013.01); *G01N 2021/399* (2013.01)

(58) Field of Classification Search
None
See application file for complete search history.

(56) References Cited

U.S. PATENT DOCUMENTS

| | | | |
|---|---|---|---|
| 4,728,189 A * | 3/1988 | Oishi | G01N 21/3103 356/307 |
| 5,173,749 A | 12/1992 | Tell et al. | |
| 6,115,673 A | 9/2000 | Malin et al. | |
| 6,610,982 B2 | 8/2003 | Hoult | |
| 6,687,620 B1 | 2/2004 | Haaland et al. | |
| 6,839,658 B2 | 1/2005 | Causse et al. | |
| 6,983,176 B2 | 1/2006 | Gardner et al. | |
| 7,003,436 B1 | 2/2006 | Kane et al. | |
| 7,092,832 B2 | 8/2006 | Brown | |
| 7,092,852 B1 | 8/2006 | Kane et al. | |
| 8,027,033 B2 | 9/2011 | Lipson et al. | |
| 8,711,357 B2 | 4/2014 | Liu et al. | |

(Continued)

OTHER PUBLICATIONS

P. Werle et al., "Real-time signal-processing concepts for trace-gas analysis by diode-laser spectroscopy", Optical Engineering, vol. 33, No. 9, Sep. 1994, pp. 3093-3105.

(Continued)

*Primary Examiner* — Reema Patel
*Assistant Examiner* — Steven M Christopher
(74) *Attorney, Agent, or Firm* — Barnes & Thornburg LLP

(57) ABSTRACT

A method for spectral interpretation in absorption spectroscopy uses a nonlinear spectral fitting algorithm for interpretation of spectral features in complex absorption spectra. The algorithm combines two spectral modeling techniques for generating spectral models to be used in the curve fitting process: a line-shape model and a basis-set model. The selected models for all gas components are additively combined using a least squares minimization, allowing for quantification of multiple species simultaneously.

13 Claims, 1 Drawing Sheet

(56) References Cited

U.S. PATENT DOCUMENTS

| | | | |
|---|---|---|---|
| 8,987,686 B2 | 3/2015 | Rizkallah et al. | |
| 2012/0170043 A1* | 7/2012 | Rao | G01N 21/39 356/437 |
| 2013/0267035 A1* | 10/2013 | Russo | G01N 21/75 436/171 |
| 2015/0099274 A1* | 4/2015 | Axelrod | C12M 41/34 435/39 |

OTHER PUBLICATIONS

Printouts-Wikipedia, Least-squares spectral analysis, 7 pages.
S. Ball et al., "Broadband Cavity Ring-Down Spectroscopy", Cavity Ring-Down Spectroscopy: Techniques and Applications, 2009, Blackwell Publishing Ltd., Chapter 3, 32 pages.
W. Demtroder, Laser Spectroscopy, Basic Principles vol. 1, 4th Ed. Springer, 40 pages.
W. Demtroder, Laser Spectroscopy, Experimental Techniques vol. 2, 4th Ed., Springer, 26 pages.

* cited by examiner

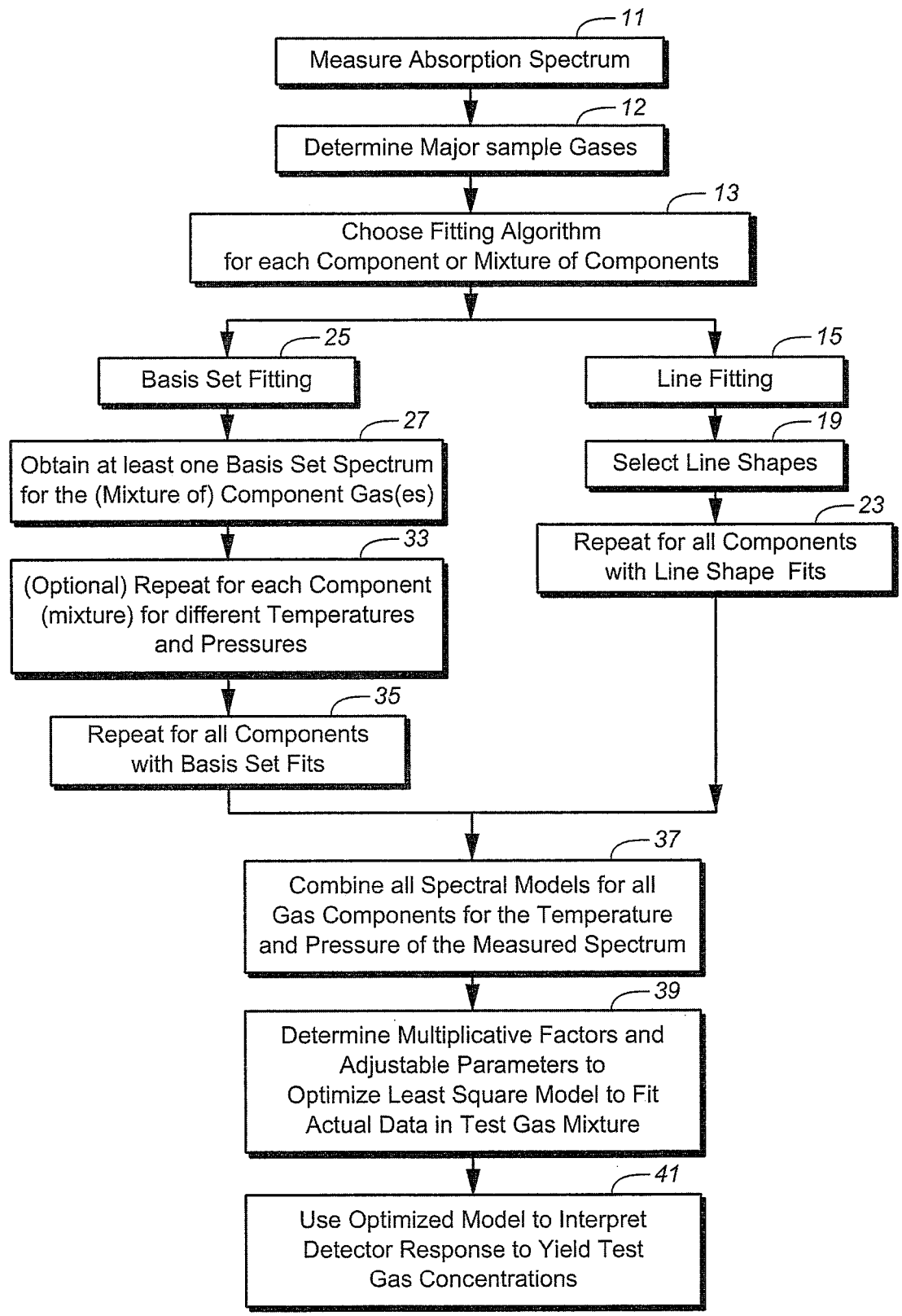

SPECTRAL MODELING FOR COMPLEX ABSORPTION SPECTRUM INTERPRETATION

TECHNICAL FIELD

The invention relates to absorption spectroscopy and in particular to gas concentration and isotope measurements in instruments such as tunable diode laser absorption spectroscopy devices (TDLAS) and other beam spectroscopy instruments measuring absorption spectra from complex test gas mixes.

BACKGROUND ART

In absorption spectroscopy, such as TDLAS and cavity enhanced spectroscopy, an absorption spectrum measured by an instrument allows the calculation of gas and/or isotope concentration by interpretation of spectral data. Spectral data is collected from the observed response of a detector to an optical beam that has interacted with a test gas. The interpretation of the spectrum can be as simple as measuring the height of detector peaks, but is generally more complicated, requiring an algorithm that models the spectrum. TDLAS, including all types of cavity enhanced spectroscopy, generally involves measuring an absorption spectrum followed by a numerical treatment of the measured spectrum to extract the relevant concentration and/or isotope data. (See, for example, Wolfgang Demtröder, Laser Spectroscopy, $2^{nd}$ ed., 1996.)

In general, as spectral complexity increases, the complexity of the spectral treatment/fitting also increases. Currently, the most common method for numerical processing of absorption spectra is fitting using one of a number of absorption line-shape models, including Lorentzian, Gaussian, Voigt, Galatry, speed dependent Voigt, and Rautian. These line shape models utilize a number of adjustable parameters to match the height and width of a theoretical shape feature to those of the measured absorption feature using an iterated, least-squares approach. These line-shape models also have the advantage of being easily adjusted for temperature and pressure variations in the sample. However, line-shape models sometimes fail for complicated absorption spectra, as they are unable to robustly distinguish between closely spaced absorption features. Even if the fit can distinguish between strongly overlapping features, the possibility of non-unique least-squares minimizations exist. Furthermore, the fits are often computationally impractical or do not converge reliably. Conventional spectral models have difficulty fitting complicated spectra, that involve multiple absorption lines and multiple absorbing species. This is a particularly challenging problem when attempting to measure trace compounds in mixtures of strongly absorbing species, or absorbing features where it is difficult to measure a baseline (no absorption) value. In addition, line-shape models can be challenging to implement when the optimal line shape is not known or when the absorption parameters are either not known or appear to be incorrect in the literature.

For more complicated absorption spectra, the current method of choice is a basis-set model, which uses measured spectral information (referred to as basis spectra) rather than simulating the spectral information using a line-shape model. Typically, a single-component mixture (e.g. a sample gas in a nonabsorbing background such as $N_2$) is introduced into the absorption spectrometer and the spectrum of that single component is measured. A thorough basis-set treatment requires collection of a matrix of basis-set spectra covering the temperature and pressure ranges over which the absorption measurements will be made. This process is repeated for each of the absorbing gases that are expected to be present in the measured gas matrix. Alternatively, basis-set spectra can be collected for mixtures of gases which are expected to remain at constant concentration ratios within the test gas mixture. In this way, a library of basis spectra for each component or mixture of components is built. Then, the measured spectrum from the analyzed gas is processed using a least-squares fitting algorithm that generates a linear combination of the basis set spectra. The multiplicative factor for each basis spectrum is then used to determine the concentration of each of the subcomponents given the known concentration(s) at which the basis spectrum was collected.

The basis-set model method has the disadvantage that, especially for a complicated mixture, many basis set spectra must be individually measured. The basis-set method is also limited by the availability and purity of individual gases for measurement of the basis sets and by the non-uniqueness of least-squares minimization solutions for minimizations with a very large number of basis set spectra. Furthermore, for measurements made in extreme environments such as cross-stack experiments, it is often difficult to measure basis set spectra at the temperature and pressure conditions of interest. Finally, system effects and the presence of unknown absorbers can cause basis-set methods to be impractical and/or imprecise.

Previous work by Haaland et al. has attempted to address the last of these issues by adding additional estimated basis spectra to the measured basis spectra (U.S. Pat. Nos. 6,415,233 and 6,687,620). In these techniques, an estimate of a source of spectral variation, often the residuals of a classical least squares fit, is used to create an additional basis spectrum which is then used in addition to measured basis spectra in a classical least square treatment of the spectral data. Kane et al. have used a comparable approach for treatment of background signals where a singular value decomposition is used to estimate basis spectra for background signals (U.S. Pat. Nos. 7,003,436 and 7,092,852). In both of these approaches, estimated spectra are used only for those components of the mixture or other spectral features which the instruments are unable to measure.

A problem that exists is that there is not a way to interpret complicated absorption spectra except for a tedious basis-set spectral fit, with all of the associated drawbacks of a basis-set approach. An object of the invention was to produce a faster and more easily implemented approach based on the characteristics of the sample gas mixture and its absorption spectrum for absorption spectral interpretation to measure test gas and/or isotope concentrations in gas mixtures with complicated spectra.

SUMMARY OF INVENTION

The above object has been met with a spectral interpretation method for gas mixtures that models an absorption spectrum as a combination of different spectral models. In most applications of absorption spectroscopy, the composition of sample gases is generally known. For example in atmospheric studies, pollutant gases are known, depending on locality, but concentrations are not known. Similarly, in industrial stack monitoring from manufacturing or production processes, gases in the stack are known but concentrations are usually not known. If however gas mixture components are unknown, it is generally possible to perform a preliminary measurement to identify gas components in the mixture. Techniques available for determining gas components include but are not limited to gas chromatography, mass spectrometry, Fourier transform infrared spectroscopy, and absorption spectroscopy. It is not necessary to know the identities of any non-absorbing species in the gas mixture and it is possible to model unknown species producing small absorptions with a line-shape model. The invention uses an additive combination of basis-set data for some components of a test gas mix and a simulated line-shape model for other components of the test gas mix. The additive combination generates spectral models to be used in the least-squares fitting algorithm.

Basis-set data are used for gas components whose spectra are difficult to accurately model using a line-shape model, such as those that have overlapping or closely spaced spectral lines and/or poor return to a nonabsorbing background. Basis sets are also measured for gas components whose spectra are expected or known to be sufficiently complex to be computationally difficult to model using a line-shape model. For example, using an Intel Atom 1.8 GHz processor, fitting a 1000 point absorption spectrum with a baseline and 15 Voigt peaks with only 6 total floating parameters requires approximately 100 ms of computation time. More complicated spectra and faster analysis needs will suggest basis-set modeling, while improvements in computational speed will reduce the need for basis-set modeling for computational reasons. Basis sets can also be used for gas species for which published spectral parameters are unavailable.

For species anticipated or known to be in the measured gas mixture where the spectra are well modeled by a line-shape model, basis sets are unnecessary. Models for the spectra of these gas species are generated as a combination of individual absorption lines using a selected Voigt, Gaussian, Lorentzian, Galatry, time dependent Voigt, Rautian or other appropriate line-shape model or combination of models. The addition of these two different types of models (basis set+line shape), the appropriate type chosen for each gas component based on its spectral features, is then used as the model function for a least-squares minimization, and the multiplicative factors for the basis spectra, as well as the individual line parameters, are varied to minimize the least-squares residuals. The invention reduces the number of basis spectra which must be collected thereby accelerating interpretation of concentrations of a test gas mixture. The invention also reduces computational load associated with a large number of line-shape spectral models while retaining the excellent isolation of species of interest that is a key feature of line-shape models. Once the hybrid model is established to characterize detector response to the test gas mixture, gas and/or isotope concentrations are established by calibration.

DESCRIPTION OF THE FIGURES

FIG. 1 is a diagram of a spectral interpretation approach for a test gas mix creating a complex absorption spectrum.

DETAILED DESCRIPTION

With reference to FIG. 1, block 11 shows that the absorption spectrum of the test mix is measured and data is stored. In accordance with the present invention, the absorption spectrum will be sufficiently complex as to be difficult to interpret using the standard simple line-shape model. Measurement may be completed using a TDLAS spectrometer or similar instrument. Analog absorption data is converted to the frequency domain and stored in a computer where known spectral components can be identified.

Block 12 shows that gases in a test mix are determined, such as by chemical tests, gas chromatography, mass spectrometry, Fourier transform infrared spectroscopy, absorption spectroscopy, source knowledge, regulatory filings, government tests, or historical information and review. Knowledge of the major absorbing test gas mix components is essential; however knowledge of non-absorbing and minor species, while helpful, is not essential. The test mix in block 12 is determined to have a known combination of component gases with complex spectra.

A basis-set or line-shape fitting model is then chosen for each of the known components, or mixture of components if applicable, as indicated by block 13. Any gas component that is expected to be successfully modeled by a line-shape model is treated accordingly, as indicated by block 15. In that situation, reference can be made, if available, to a publication or database, such as the HITRAN database, that contains absorption spectral data for many molecular species associated with atmospheric absorption. Once spectral line parameters are identified for a component gas, a common line-shape model is selected for the lines, selected from Gaussian, Lorentzian, Galatry, speed dependent Voigt, or Rautian models, as shown in block 19. The whole procedure is repeated for each component gas modeled with a line shape, indicated by block 23.

Any gas component or mixture having a complex spectrum is modeled by a basis-set model, indicated by block 25. In a basis-fit spectral model, spectral information for each component is acquired, as indicated by block 27. Acquisition of basis-set spectra may consist of measuring new basis-set spectra or alternatively may consist of reading previously collected basis-set spectra from a file. The process is optionally repeated for different temperatures and pressures for each component, indicated by block 33. The whole procedure is repeated for each component gas or mixture with complex spectrum, such as a spectrum for which line-shape modeling is known or expected to be unsatisfactory, indicated by block 35. By obtaining basis spectra at a variety of temperatures and/or pressures, the basis spectra can be interpolated in temperature and pressure space. This is an advantage because basis spectra are generally static and cannot be adjusted for temperature and pressure variations in the same way that line-shape models can be adjusted. Accounting for the temperature and pressure variations results in higher overall sensor accuracy.

A linear combination of the spectral models for all gas components is created in block 37. The multiplicative factors for all spectral models and adjustable parameters for line-shape models are varied to optimize fit to actual data using a least square minimization, indicated by block 39. The least-squares modeling algorithm may be selected, for example, from any of Levenberg-Marquardt, classical least squares, and partial least squares. Once a least squares fit is achieved, the optimized model is used to interpret detector response to test gas and/or isotope concentrations, indicated by block 41.

An example of an application of this invention would be the measurement of a trace component, such as $H_2S$, in a complicated gas mixture, such as natural gas. In this case, the $H_2S$ absorption would be modeled using a standard line-shape model such as a Voigt. Each of the components of natural gas (or a mixture of components) which absorb in the spectral region of the experiment would be measured to produce basis-set spectra for natural gas components. All together these spectra would comprise the basis set. Finally, the linear combination of the basis set and the line-shape model would be used as the model function in the least-squares fitting algorithm. The multiplicative factors from the basis-set spectra and the adjustable parameters from the line-shape function(s) would then be used in their usual manners to calculate the concentrations of the absorbing species.

If the nature of a test gas measurement suggests that temperature and/or pressure fluctuations will be significant to the spectroscopy, then additional basis spectra would be recorded at differing temperatures and/or pressures. In this case, however, not all of the basis functions are used in every least-squares fitting routine. The basis sets that are recorded at temperatures and pressures closest to the actual conditions of the measured gas would be used. Or alternatively, one can interpolate between basis functions to create a basis function for each temperature or pressure of interest.

What is claimed is:

1. A spectral line interpretation method determining gas component concentrations in a complex gas mixture using an absorption spectroscope apparatus, the method comprising:
    measuring absorption spectra from a sample gas mixture having a difficult-to-interpret spectrum;
    determining major absorbing gas components of the sample gas mixture;
    modeling each sample gas component that has simple spectral lines with a calculated spectrum using a selected line-shape model;
    modeling each sample gas component that has complex spectral lines with basis-set spectra obtained from previous measurements of known gases at multiple different temperatures and pressures, including interpolating the basis-set spectra obtained from previous measurements of known gases to determine a basis-set spectra associated with the sample gas component at a present temperature and pressure of the sample gas component;
    additively combining selected line shapes of simple spectral lines with basis sets with multiplicative factors applied for each gas component; and
    varying multiplicative factors to optimize a least-squares minimization of the additively combined spectral lines to fit measured spectral data of a complex gas mixture, a best fit of multiplicative factors corresponding to a set of concentrations of the respective sample gas components.

2. The method of claim 1 wherein measurement of the absorption spectra is made by laser spectroscopy.

3. The method of claim 2 wherein measurement of the absorption spectra is made by tunable diode laser absorption spectroscopy (TDLAS).

4. The method of claim 3 wherein measurement of the absorption spectra is made by cavity enhanced absorption spectroscopy (CEAS), including but not limited to integrated cavity output spectroscopy (ICOS), cavity ring-down spectroscopy (CRDS), and noise-immune cavity-enhanced optical heterodyne molecular spectroscopy (NICE-OHMS).

5. The method of claim 1 wherein the method of determining gas components of the gas mixture is by gas chromatography, mass spectrometry, Fourier transform infrared spectroscopy, absorption spectroscopy, or chemical test.

6. The method of claim 1 wherein the method of determining gas component of the gas mixture is by historical review.

7. The method of claim 1 further defined by obtaining the relevant spectral line parameters for the line shape fitting from a database.

8. The method of claim 1 wherein the line shape model is selected from the group consisting of Lorentzian, Gaussian, Voigt, speed dependent Voigt, Galatry and Rautian line shapes or an appropriate combination of line shapes.

9. The method of claim 1 wherein a basis-set spectrum for each selected component is measured using the instrument.

10. The method of claim 1 wherein basis-set spectra are utilized from a historical database.

11. The method of claim 1 wherein the best fit of multiplicative factors further quantifies isotope ratios of the sample gas components.

12. The method of claim 1 wherein the least squares modeling is selected from the group consisting of Levenberg-Marquardt, classical least squares, and partial least squares.

13. The method of claim 1 further comprising determining whether temperature or pressure fluctuations will cause a predefined amount of variance in the determination of the gas component concentrations.

* * * * *